US006498285B1

(12) United States Patent
Ebert

(10) Patent No.: US 6,498,285 B1
(45) Date of Patent: Dec. 24, 2002

(54) METHODS FOR PRODUCING TRANSGENIC PIGS BY MICROINJECTING A BLASTOMERE

(75) Inventor: Karl M. Ebert, Millbury, MA (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 0 days.

(21) Appl. No.: 09/129,395

(22) Filed: Aug. 5, 1998

Related U.S. Application Data

(60) Provisional application No. 60/054,988, filed on Aug. 6, 1997.

(51) Int. Cl.[7] ........................ C12N 15/00; A01K 67/027
(52) U.S. Cl. .......................................... 800/25; 800/17
(58) Field of Search ............................ 800/21, 22, 25, 800/17, 15, 16, 14; 435/455, 325

(56) References Cited

U.S. PATENT DOCUMENTS

| 4,736,866 A | 4/1988 | Leder et al. ................... 800/1 |
| 4,873,191 A | 10/1989 | Wagner et al. ............ 435/172.3 |
| 5,573,940 A | 11/1996 | Sims et al. ............... 435/240.2 |
| 5,624,837 A | 4/1997 | Fodor et al. ................. 435/325 |
| 5,627,264 A | 5/1997 | Fodor et al. ................. 530/350 |

FOREIGN PATENT DOCUMENTS

| WO | 9211757 | 9/1992 |
| WO | 9504756 | 2/1995 |
| WO | 9523512 | 9/1995 |
| WO | 9534202 | 12/1995 |

OTHER PUBLICATIONS

Sparks et al. Effects of Tem of Deoxyribonucleic Acid Microinjection of Gene Detection and In Vitro Development of Bovine Embryos. Journal of Diary Science. 1994, vol. 77, pp. 718–724.*
Niemann et al., Journal of Reproduction and Fertility, vol. 48, pp. 75–94, 1993.*
Sparks et al., Journal of Dairy Science, vol. 77, pp. 718–724, Mar. 1994.*
Wall, Theriogenology, vol. 45, pp. 57–68, 1996.*
Mullins et al., Journal of Clinical Investigations, vol. 98, No. 11, pp. S37–S40, 1996.*
Gordan et al., "Genetic transformation of mouse embryos by microinjection of purified DNA", Nat;. Acad. Sci. USA, 77:7380–7384 (1980).
Low, M.J. et al., "Cryptic human growth hormone gene sequences direct gonadotroph–specific expression in transgenic mice" Molecular Endocrinology; 3:2028–2033 (1989).
Martin et al., "Production of transgenic swine", Transgenic Animal Technology: A Laboratory Handbook, Carl A Pinkert, ed., Academic Press; 315–388 (1994).

Karp G. et al., RNA synthesis in the preimplantation rabbit embryo: radioautographic analysis Dev Biol,; 31:404–408 (1973).
Geukens et al., "Ultrastructural and autoradiographic studies of nucleolar development and rDNA transcription in preimplantation mouse embryos" Cell Different; 14:125–134 (1984).
Camous, S. et al., "Autoradiographic detection of the earliest stage of [3H]—uridine incorporation into the cow embryo" Biol Cell; 58:195–200 (1987).
Tomanek, M. et al., "Genome reactivation in developing early pig embryos: an ultrastructural an autoradiographic analysis" Anat Embryol; 180:309–316 (1989).
Brinster et al.; Proc. "Factors affecting the efficiency of introducing foreign DNA into mice by microinjecting eggs" Natl. Acad. Sci. 82:4438–4442 (1985).
Ebert et al.; Embryol. "Translation stability of ovalbumin messenger RNA injected into growing oocytes and fertilized ova of mice" Exp. Morph. 84:91–103 (1984).
Jura et al. "In vitro and in vivo development of bovine embryos from zygotes and 2–cell embryos microninjected with exogenous DNA" Theriogenology 41:1259–1266 (1994).
Pursel et al. "Effects of transferred ova per recipient and dual use of donors as recipients on production of transgenic swine" Theiriogenology 46:201–209 (1996).
Pursel et al., "Effect of ovum cleavage stage at microinjection on embryonic survival and gene integration in pigs" Proc Intl Cong Anim Reprod Artif Insem 11:480a–480b (1988).
Pursel et al., "Expression and performance in transgenic pigs" J Reprod Fert Sup 40:235–245 (1990).
Pursel et al., "Integration expression and germ–line transmission of growth–related genes in pigs" J Reprod Fertil Suppl; 41:77–87 (1990).
Mullins JJ et al., "Transgenesis in nonmurine species" Hypertension; 22:630–633 (1993).
Hammer RE et al., "Genetic engineering of mammalian embryos" J Anim Sci; 63:269–278 (1986).
Hammer, RE et al., "Production of transgenic rabbits, sheep and pigs by microinjection" Nature; 315:680–683 (1985).

(List continued on next page.)

Primary Examiner—Deborah Crouch

(57) ABSTRACT

A transgenic large mammal is produced by a method including the steps of obtaining one or more early embryos, selectively preparing an embryo having at least three cells, and preferably at a stage in development corresponding in time to the onset of transcription of the embryo's paternal genome, and introducing isolated nucleic acid molecules into a blastomere of the selected embryo. The introduction of isolated nucleic acid molecules into such embryos results in the generation of transgenic large mammals at a significantly increased frequency as compared to introducing isolated nucleic acid molecules into zygotes or into the blastomeres of embryos at the one or two cell stage of development.

8 Claims, No Drawings

OTHER PUBLICATIONS

Brinster, et al. "Factors affecting the efficiency of introducing foreign DNA into mice by microinjecting eggs" Proc. Natl. Acad. Sci. USA; 82:4438–4442, (1985).

Telford, N.A. et al., "Transition from maternal to embryonic control in early mammaliam development: A comparison of several species" Mol Reprod Dev; 26:90–100 (1990).

Berg et al., "Uberprufung verschiedener akrosomfarbungen zur qualitatsbeuteilung von und tiefgefrierperma des pferdes" Zuchthyg; 24:184–189 (1989).

Krisher et al., "Development of procine embryos from the one–cell stage to blastocyst in mouse oviducts maintained in organ culture" J Exp Zool; 249:235–239 (1989).

Yoshida M. et al., "Effect of maturation media on male pronucleu formation in pig oocytes matured in vitro" Mol Reprod Dev 31:68–71 (1992).

Hagen et al., "Development of one–cell porcine embryos to the blastocyst stage in simple media" J Anim Sci; 69:1147–1150 (1991).

Crozet et al., "Development competence of goat oocytes from follicles of different size categories following maturation, fertilization and culture in vitro" J Reprod Fertil; 103:293–298 (1995).

Selgrath et al. "Collection and transfer of microinjectable embryos from dairy goats" Theriogenology 34:1195–1205 (1990).

Hammer et al. "Production of transgenic rabbits, sheep and pigs by microinjection" Nature 315:680–683 (1985).

Palmiter et al. "Germ–line transformation of mice" Rev. Genet. 20:465–499 (1986).

Tian–Qiang Sun et al. "Human artifical episomal chromosomes for cloning large DNA fragments in human cells" Nature Genetics, 8:33–41 (1994).

Ebert et al. "Rabbit a–globin messenger RNA translation by the mouse ovum" Embryl Exp Morphol, 74:159–168 (1983).

* cited by examiner

METHODS FOR PRODUCING TRANSGENIC PIGS BY MICROINJECTING A BLASTOMERE

This application claims the benefit of U.S. Provisional Application 60/054,988, filed Aug. 6 1997.

BACKGROUND OF THE INVENTION

The first successful production of a transgenic mammal was accomplished using mice (Gordon et al., "Genetic Transformation of Mouse Embryos by Microinjection of Purified DNA" *Proc. Nat;. Acad. Sci. USA*, 77:7380–7384 (1980)). Transgenic large mammals (i.e., mammals of a species in which normal mature adults of either sex may attain a body mass of at least one kilogram) have also been produced, albeit with greater difficulty, and with a much lower frequency of transgenic offspring being obtained. The production of transgenic large mammals, including agriculturally valuable livestock, has thus been hindered by a low frequency of success (e.g., generally less than 3% in pigs) in obtaining transgenic offspring following introduction of exogenous nucleic acid molecules into zygotes, one celled embryos, or, in some cases, two celled embryos. This relatively low frequency increases the difficulty of obtaining any particular desired transgenic large mammal, with concomitant increases in time and expense.

The successful production of a variety of different transgenic large mammals has been reported. For example, transgenic large mammals have been made in which the animal produces an exogenous protein in milk, for example, tissue plasminogen factor expressed in goats and human anti hemophilic factor IX in sheep. (See, for review, Ebert, K. M. and J. P. Selgrath, "Changes in Domestic Ungulates through Genetic Engineering" in *Animal Applications in Mammalian Development*, Cold Spring Harbor Laboratory Press, 1991. *Transgenic Animal Technology: A Laboratory Handbook*, Carl A. Pinkert, ed., Academic Press (1994). Transgenic swine have been produced which express porcine growth hormone under the control of promoter/enhancer elements originally isolated from Moloney murine leukemia virus or from cytomegalovirus (Ebert, K. M. et al., *Animal Biotechnology* 1:145–159 (1990).

Transgenic mammals are useful not only as improved agricultural stock or as a means of production for a protein, but are also valuable sources of altered cells, tissues, and organs, as well as valuable research tools, e.g., for discovering the mechanisms by which gene expression is controlled. (See, for example, Low, M. J. et al., *Molecular Endocrinology* 3:2028–2033 (1989), U.S. Pat. Nos. 5,573, 940, 5,624,837, and 5,627,264, and PCT patent publications No. WO 95/04756, WO 95/23512, and WO 95/34202, which are incorporated herein by reference).

Transgenic mammals have been produced successfully by several methods, including introducing foreign DNA into the male pro-nucleus of a zygote (each pro-nucleus comprises only one haploid chromosomal complement); see, for example, Wagner et al., U.S. Pat. No. 4,873,191 (1989), disclosing transgenic mice). See also, Brinster, R. L. et al., *Proc. Natl Acad. Sci. USA* 82:4438–4442 (1985); Leder et al., U.S. Pat. No. 4,736,866 (1988)).

Transgenic large mammals have been obtained following injection of a transgene into both one and two celled embryos (Hammer, R E et al., *Nature* 315:680–683 (1985); Hammer, R E et al., *J Anim Sci* 63:269–278 (1986); Pursel et al., *Proc Intl Cong Anim Reprod Artif Insem* 11:480a–480c (1988); Pursel et al., *J Reprod Fert Supl* 40:235–245(1990); Pursel et al., *J Reprod Fertil Suppl* 41:77–87 (1990); Mullins J J et al., *Hypertension* 22:630–633 (1993); Martin et al., "Production of Transgenic Swine" pp 315–388 in *Transgenic Animal Technology: A Laboratory Handbook*, Carl A Pinkert, ed., Academic Press (1994); Seamark, R F *Reprod Fertil Dev*, 6:653–657 (1994); copending U.S. application Ser. No. 08/668,703, filed in the name of Karl M. Ebert on Jun. 24, 1996.

As a consequence of the low frequency with which transgenic large mammals have been obtained, new techniques that will allow a higher frequency of success in obtaining transgenic large mammals would be of great value, and are actively being sought.

SUMMARY OF THE INVENTION AND DESCRIPTION OF PREFERRED EMBODIMENTS

The present invention provides methods of making transgenic large mammals that generate a higher frequency of transgenic offspring than has been heretofore achievable. These methods involve procedures in which at least one embryo is prepared and genetically modified. The genetic modification is accomplished by the introduction of at least one isolated nucleic acid molecule, and preferably at least one clone (i.e., a plurality of identical copies) of isolated nucleic acid molecules into an embryo.

Large Mammals: Preferred large mammals for use in the method of the invention are herbivores, and include ungulates (i.e., hoofed mammals such as pigs, cows, goats, sheep, horses, donkeys, deer, antelopes and the like) and more generally, livestock (i.e., mammals raised for agricultural purposes such as pigs, cows, goats, sheep, horses, rabbits and the like, and/or as beasts of burden such as donkeys, horses, elephants, camels, llamas, and the like). More preferable large mammals for use in the method of the invention are pigs, goats, sheep, and bovine cattle. Particularly preferred large mammals for use in the method of the invention are members of the genus Sus, with domestic pigs being the most highly preferred of these.

Embryos: In accordance with a preferred embodiment of the invention, embryos (or zygotes, which in accordance with certain aspects of the invention will be incubated in vitro and allowed to develop into embryos before genetic modification) are recovered from the reproductive tract of a donor female (e.g., a gilt or sow), typically from the oviduct or uterus of a mature, hormonally synchronized, ovulation induced female. The embryos are microscopically inspected to determine which are at the desired stage of development. Embryo development is typically measured and characterized in terms of the number of cells making up the embryo, which number is readily counted via microscopic inspection of a living embryo and increases throughout early embryonic development.

In accordance with the invention, embryos are prepared so as to provide at least one target embryo (i.e., an embryo into which at least one clone of isolated nucleic acid molecules is to be introduced). In accordance with the invention at least one of the at least one target embryos has at least three cells. Preferably the at least one target embryo that has at least three cells is obtained by preparing a group of embryos comprising the at least one target embryo that has at least three cells.

The genetic modification is accomplished by the introduction of at least one clone of isolated nucleic acid molecules into at least one blastomere of the at least one target embryo that has at least three cells. A blastomere is any of the cells of a multi-celled pre-gastrulation embryo, which cells each comprise a diploid nucleus. The at least one clone of isolated nucleic acid molecules preferably comprises at least one transgene (the at least one transgene-comprising clone being referred to hereinafter as a "transgene clone")

Preferably at least one clone of isolated nucleic acid molecules is introduced into a plurality of the blastomeres of each multi-cellular embryo in the group of embryos. More preferably the at least one clone of isolated nucleic acid molecules is introduced into the diploid nucleus of a blastomere of a target embryo that has at least three cells.

In accordance with certain of the preferred embodiments of the invention, at least one target embryo in the group of embryos is a target embryo comprising at least four cells. Preferably the target embryo comprising at least four cells is modified by the introduction of a transgene clone into at least one blastomere of the target embryo.

A preferred target embryo is a porcine embryo comprising at least three or at least four cells.

In accordance with certain of the preferred embodiments of the invention, at least one target embryo in the group of embryos is a target embryo comprising at least five or at least six cells. Preferably the target embryo comprising at least five or at least six cells is modified by the introduction of a transgene clone into at least one blastomere of the target embryo.

In accordance with certain of the preferred embodiments of the invention, at least one target embryo in the group of embryos is a target embryo comprising at least seven or at least eight cells. Preferably the target embryo comprising at least seven or at least eight cells is modified by the introduction of a transgene clone into at least one blastomere of the target embryo. A preferred target embryo comprising at least seven or at least eight cells is a bovine embryo.

In additional embodiments of the invention, at least one clone of isolated nucleic acid molecules is introduced into at least one embryo of a group of embryos and the criteria for target embryos are further limited so that the at least one clone of isolated nucleic acid molecules is not introduced into any embryos that do not contain at least two blastomeres. In certain embodiments of this subset of preferred embodiments, these criteria are additionally limited so that the at least one clone of isolated nucleic acid molecules is not introduced into any embryos that do not contain at least three blastomeres. In certain others of this subset of preferred embodiments, these criteria are also limited so that the at least one clone of isolated nucleic acid molecules is not introduced into any embryos that do not contain at least four blastomeres. In certain others of this subset of preferred embodiments, these criteria are also limited so that the at least one clone of isolated nucleic acid molecules is not introduced into any embryos that do not contain at least five or at least six blastomeres. In certain others of this subset of preferred embodiments, these criteria are additionally limited so that the at least one clone of isolated nucleic acid molecules is not introduced into any embryos that do not contain at least seven or at least eight blastomeres. In the embodiments where all of the target embryos comprise at least seven or at least eight blastomeres, a preferred target embryo is a bovine embryo.

Paternal Genome Activation: In accordance with a particularly preferred embodiment of the invention, the target embryo that has at least three cells is obtained and prepared in such a way that at least one clone of isolated nucleic acid molecules is introduced into one or more blastomeres having a paternal genome (the portion of a diploid embryo's genome contributed by the sperm at fertilization) at a stage in the development of the embryo that is within one cell division of the point at which transcription of the paternal genome of the one or more blastomeres is initiated. This point in development may vary from species to species, but is believed to be generally uniform within a particular species of mammal.

Methods for determining the onset of transcription of the paternal genome in an embryo of any particular species of mammal are well known in the art. See, for example, Karp, G. et al. *Dev Biol*, 31:404–408 (1973); Geuskens et al. *Cell. Different.*, 14:125–134 (1984); Davidson, E. H. *Gene Activity In Early Development*, 3rd edn. Academic Press, N.Y. (1986); Camous, S. et al. *Biol Cell*, 58:195–200 (1987); Tomanek, M. et al., et al. *Anat Embryol*, 180:309–316 (1989); and Telford, N. A. et al. *Mol Reprod Dev*, 26:90–100 (1990).

Embryo Culture: In certain of the preferred embodiments of the invention, embryos are harvested from a donor female and the at least one clone of isolated nucleic acid molecules is introduced into the blastomeres of only those embryos that have reached the desired stage of development (as indicated by the number of blastomeres making up the embryo), while those harvested embryos that have not yet reached the desired stage of development are maintained in culture until one or more cell divisions have occurred and at least one of the cultured embryos has reached the desired stage of development, after which point at least one clone of isolated nucleic acid molecules is introduced into at least one blastomere of the at least one cultured embryo.

Timing of Embryo Harvest: In accordance with certain preferred embodiments of the invention, embryos are harvested at a time after fertilization when at least one of the harvested embryos has a total number of blastomeres corresponding to the stage of development at which transcription of the paternal genome begins in that species. Preferably, embryos are harvested at a time after fertilization when the majority of the harvested embryos each has at least 2 blastomeres. In a particularly preferred embodiment, the majority of embryos each has a total number of blastomeres corresponding to a stage of development within one cell division of the point in development at which transcription of the paternal genome begins in that species. Additionally, the embryos may be characterized by being at a stage in development that is no earlier than one cell division before the onset of transcription of the paternal genome and is no later than one cell division after the first cell division following the onset of transcription of the paternal genome.

In general, this aspect of the invention involves embryo harvest later in gestation than is currently practiced in the art. Since gestation time in large mammals may change in response to a number of variables (e.g. seasonal changes), the optimum timing for embryo harvest in accordance with this aspect of the invention is best determined empirically, for example, as discussed in the following two paragraphs, where particulars of carrying out this aspect of the invention in pigs are discussed.

In pigs, as discussed above, the embryos to be genetically altered are preferably three- or four-cell embryos. Such three- or four-cell pig embryos can be collected by flushing the oviduct or the uterus of naturally inseminated (mated) or artificially inseminated gilts or sows 1.5 to 2.5 days after insemination, preferably about 48 hours after insemination, as described below in Example 1.

Typically, a cohort plurality of young sexually mature female large mammals (e.g., in pigs, gilts or sows, preferably gilts—non-pregnant nulliparous female pigs), are concurrently hormonally synchronized and preferably are then concurrently (typically one after another in prompt succession) inseminated. Preferably each female being prepared as an embryo donor is repeatedly inseminated, for example as described below in Example 1. By harvesting and microscopically inspecting embryos from a single female donor of the cohort so as to determine the number of cells per embryo, a skilled worker will readily be able to determine the stage of development of the harvested embryos and thereby determine when to harvest embryos from the remainder of the cohort so as to obtain the maximal yield of embryos at the desired stage of development.

In Vitro Development of Embryos: In accordance with certain preferred embodiments of the invention, a harvested embryo that has not yet reached the desired stage of development is incubated under appropriate culture conditions until it reaches the desired stage (at which point, in accordance with the invention, the embryo comprises at least three cells), at which time at least one clone of isolated nucleic acid molecules is introduced into one or preferably more than one of the blastomeres of the embryo. Culture conditions for embryos of large mammals have been described (see, for example, Berg et al., *Zuchthyg,* 24:184–189 (1989); Krisher et al., *J Exp Zool,* 249:235–239 (1989); Yoshida M, et al., *Mol Reprod Dev* 31:68–71 (1992); Hagen et al., *J Anim Sci,* 69:1147–1150 (1991); Crozet et al., *J Reprod Fertil,* 103:293–298 (1995)).

Development of the Transgenic Animal: After the at least one clone of isolated nucleic acid molecules is introduced into the at least one blastomere, the embryo is placed in an environment that will provide appropriate conditions for the development of the animal. Preferably the environment will allow for progression through embryonic and fetal development to term. Most preferably the environment is the reproductive tract of a female animal of the same species of animal as the embryo.

ADDITIONAL ASPECTS OF THE INVENTION

Introduction

A transgenic mammal is an mammal which has been engineered by the directed genetic alteration of the embryonic cells from which the mammal or one or more of its progenitors has developed. The directed genetic alteration is accomplished by the introduction into at least one of the embryonic cells (typically a cell of an early embryo, an embryonic stem cell, or a zygote) of one or more clones of isolated nucleic acid (preferably DNA) molecules. Preferably the one or more clones of isolated nucleic acid molecules comprise one or more transgenes.

As used herein, a transgene is—1) a gene which is either synthesized in vitro or isolated from a biological source, and has been so prepared for subsequent introduction into a zygote or an embryonic cell, or—2) the transgene (as per definition 1) or a biologically replicated copy thereof that is found within a cell of an animal subsequent to the introduction of the transgene (as per definition 1) into a zygote or an embryonic cell that participates in the development of the animal or at least one of its progenitors.

As used herein, a gene is an ordered sequence of nucleotides (or the like) that has a particular function, e.g., one that is transcribed and/or translated to form a specific functional product such as a protein or RNA molecule, or has a specific regulatory function in controlling the expression of other functional nucleic acid sequences.

Successful genetic alteration results in the integration of a transgene into the replicating complement of DNA of some or all of the cells of the animal (fetal and/or adult) that develops from the zygote or embryo. Preferably, the genetic alteration has detectable effects upon the cells containing the integrated transgene(s) and/or on the entire animal, e.g., over-expression of a protein or RNA molecule in the cells, expression of an exogenous protein or RNA molecule in the cells, alteration of the metabolism of the cells, and/or an alteration of the phenotype of the animal. Expression may occur for a limited period during ontogeny or throughout the life of the animal.

General Methods

The invention relates to methods of producing transgenic large mammals by introducing one or more clones of isolated nucleic acid molecules (preferably one or more transgene clones) into at least one cell of a multicellular pre-gastrulation embryo having at least three cells, preferably at a point in the development of the embryo that is within one cell division of the point in development at which transcription of the paternal genome begins.

A zygote is a fertilized egg in which the sperm nucleus (the haploid male pro-nucleus) and the egg nucleus (the haploid female pro-nucleus) have not yet fused to form a single diploid nucleus. The fusion of the haploid male and female pro-nuclei to form a diploid nucleus marks the transition from zygote to embryo. The onset of cleavage (a specialized form of cell division that occurs early in embryonic development) and the resulting multicellular stages of embryonic development cannot occur until the individually haploid zygote pro-nuclei fuse to form a diploid embryo nucleus.

Cells of the multicellular embryo are called blastomeres until the embryo has undergone gastrulation. An early blastomere is totipotent, meaning it has the capacity (even when isolated from the other blastomeres of the embryo) to develop into a complete, normal animal, given the appropriate conditions for development. Mammalian blastomeres are believed to be totipotent at least through the 8 cell stage of development (See review article, Papaioannou, V. E. and K. M. Ebert, In: Experimental Approaches to Mammalian Embryonic Development, Pedersen, R. and J. Rossant, eds., 1986.)

In accordance with certain of the preferred embodiments of the invention, embryo collection is timed so as to obtain a group of embryos the majority of which have reached at least the two- and preferably at least the three-cell stage of development.

In some large mammals, including for example pigs, it may be desirable to culture embryos (that have not yet reached the desired stage of development) and zygotes, and to monitor cell division in culture, so as to obtain embryos at the desired stage of development.

Any technique which allows for the addition of nucleic acid molecules into a blastomere can be utilized to accomplish the genetic modification of the target embryo so long as it is not destructive to the cell membrane, nuclear membrane or other essential structures of the blastomere, or to the blastomere in general. Such techniques include, but are not limited to, microinjection (e.g., into diploid nuclei), lipofection, gene gun techniques, and electroporation. Preferably, the isolated nucleic acid molecules are introduced into the diploid nucleus of the blastomere by microinjection.

The production of a transgenic mammal typically involves the use of a solution comprising a clone of isolated nucleic acid molecules, preferably comprising a transgene clone. The clone may be of biological origin (e.g., whole chromosomes, portions of chromosomes, chromosomal complexes, other forms of chromatin, plasmids, restriction fragments of plasmids, and the like) or may be synthetic or semi-synthetic nucleic acid molecules. In most cases the clone will be a transgene clone comprising a transgene transcription unit. Such a unit typically includes: 1) a promoter, 2) a transgene, and 3) a polyadenylation signal sequence. Other sequences, such as enhancer and intron sequences, can also be included if desired, e.g., to achieve increased gene expression.

The transgene transcription unit can be conveniently prepared, for example, by isolating a restriction fragment of a plasmid vector which expresses the protein of interest in mammalian cells. Preferably, the restriction fragment is free of sequences which direct replication in bacterial host cells (i.e., bacterial origin of replication sequences) since such sequences are believed to have deleterious effects on embryo viability. Nonetheless, a clone of an intact plasmid (a circular or linearized but unfragmented plasmid) although less preferred, may be used as the clone of isolated nucleic acid molecules to be introduced into an embryo blastomere in accordance with the invention. Thus, for example, genomic DNA or cDNA constructs may be injected in linear or supercoiled form.

With the exception of the lower limit imposed by the sizes of the fundamental building blocks from which they are made up (e.g., nucleotides, nucleosides, and the like), the size of the nucleic acid molecules to be introduced into a blastomere in accordance with the invention is not critical. This can therefore vary with the length of the nucleic acid sequence or sequences desired to be introduced. The usual size of a nucleic acid molecule to be introduced into a blastomere will be long enough to include at least one functional gene to be transferred, and may typically range from a few kb to on the order of 30 kb. Cosmids, YACs, and the like may be constructed so as to introduce nucleic acid molecules of up to hundreds of kb into a blastomere.

As an alternative to introducing one or more isolated clones of nucleic acid molecules that do not carry a functional eukaryotic origin of replication, and therefore must generally rely on integration into a chromosome or episome which has such an origin so as to be replicated during the cell division cycle, the transgene clone may be introduced as an artificial episomal chromosome (Sun, T-Q. et al., *Nature Genetics* 8:33–41 (1994)). Other types of natural or, preferably, artificial chromosomes may also be used as transgene clones in the methods of the invention if desired.

If a clone of isolated nucleic acid molecules is to be introduced into a blastomere by microinjection, it is preferably extensively purified first, for example, plasmids or restriction fragments may be purified by gel isolation followed by passage over an ion exchange resin such as an ELUTIP column (Schleicher & Schuell, Keene, N.H.), followed by dialysis against pyrogen free injection buffer (e.g., 10 mM Tris, pH7.4+0.1 mM EDTA in pyrogen free water). If the clone of isolated nucleic acid molecules is a chromosome or chromosome fragment clone, the purification method will preferably not separate the chromosomal proteins from the chromosomal nucleic acid molecules. In such cases, preferred purification methods include ultracentrifugation (e.g., sucrose gradient centrifugation) and centrifugal elutriation.

The microinjection of zygote pro-nuclei or nuclei of one cell or, less commonly, two cell embryos to make transgenic mammals is widely practiced by those of skill in the art. As an example, transgenic swine are routinely produced by the microinjection of a transgene transcription unit into pig zygotes or embryos. See, for example, PCT Publication No. WO92/11757; Martin et al., "Production of Transgenic Swine" pp 315–388 in *Transgenic Animal Technology: A Laboratory Handbook,* Carl A Pinkert, ed., Academic Press (1994).

Production of transgenic animals: At least one embryo (and preferably a plurality of embryos) is prepared. At least one (and preferably a majority) of the embryos has at least three cells. Preferably at least one (and more preferably a majority) of the embryos is at a stage of development within no more than one cell division from the stage at which transcription of the paternal genome begins.

The embryos are placed into a vessel (e.g., 1.5 ml microfuge tube) containing a small volume (e.g., approximately 0.5 ml) of a suitable embryo transfer medium (e.g., phosphate buffered saline with 10% fetal calf serum). Embryos of large mammals that have opaque embryos (e.g., pigs) are typically centrifuged to allow the visualization of the blastomere nuclei, e.g., for 4 minutes at 13,000×g in a microcentrifuge. Embryos are removed from the centrifuge tube (e.g., with a drawn and polished Pasteur pipette) and placed into a small dish (e.g., a 35 mm petri dish) for examination. If the cytoplasm is still opaque with lipid such that the nuclei are not sufficiently visible to allow visual verification of nuclear injection, the embryos may be centrifuged again for about 4 minutes.

Methods of microinjecting cells, such as zygotes and embryos, are well known in the art, and are described, for example, in Brinster, R. L. et al., *Proc. Natl. Acad. Sci. USA* 82:4438–4442 (1985). Such methods are also applicable to the microinjection of blastomere nuclei.

For microinjection, embryos can be placed on a surface, such as the center of the lid of a 100 mm petri dish, in culture medium. Typically a drop of medium (approximately 100 microliters) is used. Suitable media for the microinjection procedure in multicellular pre-gastrulation embryos are, for instance, modified BMOC-2 containing HEPES salts, as described in Ebert, K. M. et al. *J. Embryol. Exp. Morph.* 84:91–103 (1984); or PBS medium supplemented with 20% fetal calf serum (Jura, J. et al. *Theriogenology* 41:12S9–1266 (1994)) or Brinster's medium plus 25 μM HEPES buffer (pH 7.4) (Brinster, R. L. et al. *Proc. Natl. Acad. Sci. USA* 82:4438–4442 (1985)). Of these, the first is most preferred. If desired, silicone oil or the like may be used to cover the drop of medium and to fill the lid to prevent the medium from evaporating.

An embryo to be injected is typically held in place by suction on a blunt holding pipet of a suitable diameter. Blastomere nuclei are then injected with a solution of isolated nucleic acid molecules via a sharp-tipped (1–2 μm diameter, for example) injector pipet (injection needle). Swelling of the nucleus can generally be observed upon successful injection. The movements of the means for holding and injecting the cells are preferably controlled by appropriate micromanipulation instruments.

The process is best observed under a microscope (preferably an inverted microscope equipped with both a heated stage and enhanced contrast optics such as Hoffman modulation optics or Nomarski optics) using suitable magnification, e.g. 200–250×. Clones of isolated nucleic acid molecules can be injected into blastomere nuclei in a volume of 1–2 pl, optimally. More or less volume may be injected if desired, up to a maximum volume that does not cause irreparable damage to the nucleus or to the cell. Concentrations of the transgene clone may vary. Preferably the concentration will vary from approximately 1 to 4 ng/μl for restriction fragments, with chromosomes and other larger molecules typically being at higher concentrations so as to adjust for the lower molarity of equivalent concentrations of such large molecules. Optimal concentrations of transgene clones to be used may be adjusted empirically, but higher integration frequencies have been observed in fertilized eggs when several hundred copies of a transgene are injected. (See, e.g., for heifers, McEvoy, T. G. et al., *J. Reprod Fert Suppl,* 43: 297–289 (1991)).

Embryos surviving the microinjection process, as judged, e.g., by microscopic observation of morphology, are preferably transferred to the reproductive tract of a recipient female shortly after introduction of the isolated nucleic acid molecules. In some instances it may be desirable for the surviving embryos to be cultured for a time and subsequently transferred. Surviving embryos are typically introduced into the oviduct or uterus, as appropriate so as to best match the developmental stage of the cultured embryo to the stage of pregnancy (or, although generally less preferred, pseudopregnancy) of the host female and the location of embryos in the reproductive tract of an animal at the corresponding stage of pregnancy). In some cases it may be more efficient to use donor females as recipients as well; i.e., subsequent to embryo collection, but while the animal is still undergoing the surgical procedure for embryo harvest, genetically altered embryos are introduced into the reproductive tract of the donor female, so as to utilize the donor as a recipeint. See, for example, Pursel et al., *Thieriogenology,* 46:201–209 (1996).

When required or desired, in vitro incubation for some period of time before transferring the embryo into an appropriate female host animal is preferably carried out with as little delay as possible. Preferably the delay is no more than 5 hours, more preferably the delay is no more than 4 hours, even more preferably the delay is no more than 3 hours, most preferably the delay is no more than 2 hours.

The host animal that serves as a surrogate mother can be any animal that can provide the appropriate hormonal and nutritional environment for the growth and development of the embryo to term. Such an animal can be a pregnant female with embryos at or close to the same stage of development as the surviving embryo or embryos to be transferred to her reproductive tract, or an animal at a stage in the estrous cycle in which the reproductive tract would be receptive to the introduction of an early embryo. For example, the estrous cycle of pigs can be hormonally synchronized using norgestomet implants, as described below in the examples.

Synchronization may also be achieved by other methods. For example, the use of ALTRENOGEST or the like in animal feed is well known in the art as a method for synchronizing large mammals. Typically, in pigs, ALTRENOGEST feeding is initiated 12–16 days following estrus and continued for 9 days, followed by the administration of Pregnant Mare's Serum Gonadotropin (PMSG) one day after last ALTRENOGEST feeding. Human Chorionic Gonadotropin (hCG) is also administered as needed in conjunction with this regimen, for example as described below in Example 1 for the norgestimet implant method. Variations of these techniques allowing their application to the synchronization of a number of large mammal species are known in the art (see, for example, Selgrath et al., *Theriogenology* 34:1195–1205 (1990)—goats; Rexroad et al., *Mol. Reprod. Dev.* 1:164–169 (1989)—sheep), Hammer et al., *Nature* 315: 680–683 (1985)—(sheep, pigs, and rabbits) as are methods for the determination of optimal protocols for large animals for which such synchronization procedures have not been described in detail.

Alternatively, in some species (e.g., in rodents), the host female can be induced to a pseudopregnant state using appropriate treatments that are known in the art.

Preferably, the surrogate mother mammal is of the same species as the embryo. Usually, this is required for the development of the embryo to term. However, some exceptions are known. For example, one species of antelope can in some cases serve as surrogate mother for gestation of an embryo of a different species of antelope (Dresser, B. L. et al., *Proc. Am. Assoc. Zool. Parks Aquar.* 166–8 (1994)).

Applications and Further Considerations

Transgenic Animals: The invention can be used to modify a species (i.e., to create a new species variant). A new species variant can be obtained when a new genotype results from the introduction of the one or more clones of isolated nucleic acid molecules into one or more blastomeres of a target embryo and the new genotype occurs in the germline cells of an animal that develops from the target embryo so that the new genotype can be transmitted to the progeny of the animal.

The invention is particularly useful in the breeding of livestock of agricultural value, to obtain new species variants having genetic makeups that result in animals exhibiting more agriculturally and/or commercially desirable characteristics.

In some cases, it may be advantageous to use the transgenic large mammal embryo as a system to test for the timing and extent of expression of certain genes during the development of the animal. This can be done using known methods in the art. One method is, for example, recovering an embryonic or fetal animal, isolating polyA+ RNA from one or more tissue types of interest, and testing the polyA+ RNA (e.g., using hybridization with a labeled nucleic acid probe under maximally stringent conditions) for the presence of sequences homologous to the transgene.

Nucleic Acid Molecules: The one or more clones of isolated nucleic acid molecules may be obtained from numerous biological sources, such as animals or plants, viruses, bacteria, or protozoa; or may be of synthetic origin. The one or more clones may be synthetic equivalents of naturally occurring genetic material or may be totally new synthetically produced genetic material. The one or more clones of isolated nucleic acid molecules can be from the same species as the blastomere into which it is to be introduced, or from a different species.

Depending upon the particular trait or traits which are desired in the animal, it will generally be necessary to include in the introduced nucleic acid molecules the controlling elements (e.g., promoters, enhancers, polyadenylation sites, transcription termination sites, ribosome binding sites, and the like) responsible for expression of the gene(s) coding for the gene product that will affect the trait.

In some cases, it may be desirable to introduce back into the same species, in unmutated form, a gene originally isolated from that species. More typically, if it is desired to introduce back into the same species a gene originally isolated from that species, the gene will have been altered (mutated) to produce a different amount of gene product and/or an altered gene product compared to that produced in normal (e.g., non-transgenic) animals. In many cases it may be desirable to introduce back into the same species a gene originally isolated from that species which has been put under the control of controlling elements, either synthetic or isolated from a different organism and/or a different gene. In some instances it may be desirable to include a control region that will activate the gene when the transgenic animal is exposed to a stimulus other than one of the natural stimuli that activate or deactivate the gene.

Techniques for obtaining segments of DNA by gene excision, splicing, synthesis, isolation, purification, cloning and the like are well known in the art. Enzymes used in such processes, vectors and hosts for cloning of recombinant nucleic acid molecules, screening and selection of desired nucleic acid molecules and detection and analysis of expression of cloned genes are also well known in the art. (See, for example, Ausubel, F. M. et al., eds. *Current Protocols in Molecular Biology*, Greene Publishing Associates and John Wiley & Sons Inc., (1997)).

The number of nucleic acid molecules which constitute the one or more clones of isolated nucleic acid molecules that is introduced into a blastomere will depend upon several factors, including (for transgene clones) the number of copies of the transgene per nucleic acid molecule. The total amount of isolated nucleic acid molecules introduced is preferably an amount which enables the integration of an isolated nucleic acid molecule into the genome of the blastomere. In cases where the one or more clones of isolated nucleic acid molecules comprise a transgene clone, total amount of isolated nucleic acid molecules introduced is preferably an amount which allows incorporation of at least one transgene of the transgene clone to occur in such a way that the at least one transgene can be expressed. Theoretically, only one copy of a particular transgene is required. However, it is preferable that numerous copies of the nucleic acid molecules which constitute transgene clone are introduced, for example, 100–1,000 copies, in order to insure that at least one copy of at least one transgene becomes integrated in a functional state.

For example, a successful result of prior art methods of injecting the male pronucleus of a zygote of a mouse with multiple copies of linear DNA nucleic acid molecules which constitute a transgene clone has been, typically, a transgenic mouse with all or some of its cells containing a tandem array of copies of the injected nucleic acid molecules (and the transgene therewithin) integrated at a single random site in one of its chromosomes (Palmiter, R. D. and R. L. Brinster Ann. Rev. Genet. 20:4 65–499 (1986)).

Generally, the chief advantage to having more than one functioning copy of each of the introduced transgenes is enhanced expression. There are also instances where more than one functional copy of the transgene clone may be undesirable, for example when a transgene works in conjunction with endogenous nucleic acid sequences of the organism to produce a particular product.

Identifying Transgenic Offspring: Cell or tissue samples may be taken from the animal developing from the embryo into which the one or more clones of isolated nucleic acid molecules has been introduced to test for the presence of the introduced nucleic acid molecules. Depending on the type of large mammal, cells obtained from the embryo, fetus, neonate, developing offspring or adult can be tested for the presence of the introduced nucleic acid molecules by well-known techniques of molecular biology. Such techniques involve, for example, obtaining a sample of DNA from cells (typically and preferably somatic cells) obtained from the fetus, neonate or developing offspring (e.g., from a segment of tail or a snippet of ear) and testing it for the presence of the introduced nucleic acid molecules. Such testing may be accomplished, for example, by nucleic acid hybridization using a specific probe, or by using oligonucleotides (e.g., as primers) for the specific amplification of the transgene, e.g., by PCR (or another amplification method), or by other suitable methods. Such additional methods may include the identification of a phenotypic effect of the introduced nucleic acid molecules. This may be identified either by detection of the appearance of a previously absent gene product or by detection of altered levels of a native gene product. Such detection may be accomplished, for example, by probing with a gene product specific antibody.

Phenotypic alterations may also be detected as alterations in the expression of other genes interacting with the one or more isolated nucleic acid molecules that have been used to produce the transgenic animal. For example, the addition of one or more transgenes in the form of a new promoter and/or controlling element, or a fragment of a promoter and/or controlling element introduced to supplement an existing promoter and/or controlling element, may effect a detectable phenotypic alteration.

Identifying Germ Line Transmission: Transgenic animals capable of germ-line transmission are particularly desirable, as they allow the creation of and perpetuation of new species variants. Such transgenic animals can be tested for by various means well known in the art, for example through the analyses of the DNA of germ cells (e.g., as described above) and/or by breeding experiments.

Additional Limitations: The physical effects of the alteration in the genome of the altered blastomere must not be so great as to destroy the viability of the blastomere. The biological limit of the number and variety of isolated nucleic acid molecules introduced will vary depending upon the particular blastomere and the functions of any transgenes incorporated in the isolated nucleic acid molecules. The genetic material of the resulting blastomere must be biologically capable of initiating and maintaining the differentiation and development of the blastomere. When the one or more clones of isolated nucleic acid molecules are in the form of chromatin, chromatinosomes, or chromosome fragments, the addition of no more than one chromosome (and, more typically, less than one chromosome, i.e., part of a chromosome) is generally preferred in order to limit the potentially deleterious effects of extra chromosomes upon cell division and viability.

EXAMPLES

Example 1

Preparation of Target Embryos

Yorkshire gilts were used for the collection and transfer of one-cell, two-cell, three-cell, and four-cell embryos. The gilts were synchronized by placing 2 SQ norgestomet implants (SYNCHRO-MATE-B; RHONE MERIEUX) subcutaneously in the ear. A single implant was introduced on day 1 followed by a second on day 10 to ensure adequate active progesterone throughout the synchronization period. On day 19 at about 11 AM both implants were removed and the donor animals were given 2000U PMSG (Calbiochem) I.M. Subsequently, donor animals were injected with 1000U hCG (Calbiochem) I.M. 56 hours post PMSG injection (on day 21 at about 7:00 PM). Donor animals were then artificially inseminated at 22 hours and 38 hours after hCG injection (at about 5 PM on day 22 and at about 9:00 AM on day 23). Embryos were collected approximately 48 hours after the second insemination under aseptic conditions. Donors were anesthetized with 2 mg/lb. of ROMPUN followed by 3 mg/lb. TELAZOL (both from Henry-Schein, Port Washington, N.Y.), with an inter-operative dose of 1 mg/lb. of TELAZOL administered as needed to maintain adequate anesthesia. A mid-line laparotomy was performed on each donor and the reproductive tract of each donor was exteriorized. Numbers of recent ovulations were counted by visual inspection of each ovary. Collection of embryos was then accomplished by cannulating the ampulla region of the oviduct and flushing the oviduct by injection of 10–15 mls of phosphate buffer saline solution from the utero-tubule junction. In those cases where the number of collected embryos from an oviduct was less than the count of ovulations from the ipsilateral ovary, uterine harvest was also carried out as follows. Approximately 30 ml of PBS was used to flush the cranial 30 cm of the uterus in a retrograde fashion toward a cannula inserted at the utero-tubule junction.

Flushings were examined under a stereomicroscope and embryos were transferred to Ham's F-12 medium containing 10% fetal calf serum and were incubated for no more than 5 hours at 37° C. in 5% $CO_2$ until the time of injection.

A total of 75 gilts were used as donors for the collection of embryos. The above regime produced an average of 32.45 ovulations and resulted in the collection of embryos as follows: 1152 one-cell (61.51%), 241 two-cell (12.87%), 50 three-cell (2.67%), 402 four-cell (21.46%), and 28 (1.49%) greater than four-cell.

Example 2
Microinjection of Pig Blastomere Nuclei

Prior to injection, embryos were centrifuged at 13,000×g for 4 minutes in an EPPENDORF microcentrifuge to visualize the blastomere nuclei. Interference contrast microscopy was used to view the nuclei and approximately 2 picoliters of DNA solution was injected into as many blastomere nuclei as possible within each developing embryo. Nuclei that were not visible were not injected. The injections were done in a droplet of modified PLG medium containing HEPES salts (modified BMOC-2; Ebert K M, et al., *J Embryol Exp Morphol*, 74, 159–168 (1983)). The injected embryos were transferred to Ham's F-12 medium containing 10% fetal calf serum and were briefly (when conveniently practicable, less than three hours) incubated at 37° C. in 5% $CO_2$ until transfer to recipient gilts.

Example 3
Transfer of Embryos into Recipient Host Gilts

Yorkshire gilts to be used as recipients were synchronized by placing 2 norgestomet implants (SYNCHRO-MATE-B; RHONE MERIEUX; Henry-Schein, Port Washington, N.Y.) subcutaneously in the ear, one each on days one and ten. On day 19 both implants were removed and the donor animals were given 1000 IU PMSG (Pregnant Mare Serum Gonadotropin, CALBIOCHEM) I.M. Subsequently, donor animals were injected with 500 IU hCG (Human Chorionic Gonadotropin, CALBIOCHEM) I.M. on day 21 (56 hours post-PMSG injection). Embryos, the majority of which had been microinjected, were transferred on day 25 under aseptic conditions. Transfer was accomplished using a sterilized 20 microliter glass pipet. The pipet was filled in three stages. First, about half the pipet volume was filled with the embryo culture medium (Ham's F-12 medium containing 10% fetal calf serum). Next, a small air bubble was drawn into the pipet. (Among the benefits provided by the air bubble in the pipet is easier handling due to the bubble's resistance to movement of the medium in the pipet, and ease of verification of transfer by visual observation of the air bubble in the oviduct.) Finally, the pipet was filled the rest of the way with about 10 microliters of embryo culture medium containing the embryos to be transferred. Transfer was then accomplished by inserting the tip of the pipet approximately 5 cm into the oviduct of the recipient gilt via the fimbrial os and expelling the embryos under positive pressure.

Throughout this application various publications, patents, and patent applications are referred to. The teachings and disclosures of these publications, patents, and patent applications in their entireties are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

What is claimed is:

1. A method for producing a transgenic pig comprising:
   a) obtaining a porcine embryo comprising at least three blastomeres;
   b) introducing at least one clone of isolated nucleic acid molecules into at least one blastomere of the embryo;
   c) transferring the embryo to a surrogate female pig;
   d) developing the embryo into at least the fetal stage; and
   e) developing the fetus into a transgenic pig.

2. The method of claim 1 wherein the embryo is a 3 cell embryo.

3. The method of claim 1 wherein the embryo is a 4 cell embryo.

4. A method for producing a transgenic pig comprising:
   a) obtaining a porcine embryo comprising at least three blastomeres, wherein the embryo is characterized by being at a stage in development that is no earlier than one cell division before the onset of transcription of the paternal genome and is no later than one cell division after the first cell division following the onset of transcription of the paternal genome;
   b) introducing at least one clone of isolated nucleic acid molecules into at least one blastomere of the embryo to produce an embryo comprising at least one modified viable blastomere;
   c) transferring the embryo comprising at least one modified viable blastomere, or one or more of any viable blastomeres descending therefrom by cleavage, to a surrogate female pig; and
   d) developing the transferred embryo into a transgenic pig.

5. The method of claim 4 wherein the embryo is selected from the group consisting of 3 cell embryos and 4 cell embryos.

6. A method for producing a transgenic pig comprising:
   a) obtaining a group of porcine embryos comprising at least one embryo that comprises at least three blastomeres;
   b) introducing at least one clone of isolated nucleic acid molecules into at least one blastomere of the at least one embryo to produce at least one modified viable blastomere;
   c) transferring the embryo comprising at least one modified viable blastomere, or one or more of any totipotent viable blastomeres descending therefrom by cleavage, to a surrogate female pig;
   d) developing the embryo into at least the fetal stage: and
   e) developing the fetus into a transgenic pig.

7. The method of claim 6 wherein the at least one embryo is a cultured embryo prepared by culturing an embryo having fewer than three blastomeres until cell division within the cultured embryo results in a cultured embryo having at least three blastomeres.

8. The method of claim 6 wherein the at least one embryo is a cultured embryo prepared by culturing a zygote until cell division within the cultured zygote results in a cultured embryo and cell division within the cultured embryo results in a cultured embryo having at least three blastomeres.

* * * * *